United States Patent
Bastide et al.

(10) Patent No.: US 10,290,377 B2
(45) Date of Patent: May 14, 2019

(54) SOCIAL HEALTH RISK ESTIMATION

(71) Applicant: International Business Machines Corporation, Armonk, NY (US)

(72) Inventors: Paul R. Bastide, Boxford, MA (US); Matthew E. Broomhall, Goffstown, NH (US); Robert E. Loredo, North Miami Beach, FL (US)

(73) Assignee: International Business Machines Corporation, Armonk, NY (US)

( * ) Notice: Subject to any disclaimer, the term of this patent is extended or adjusted under 35 U.S.C. 154(b) by 384 days.

(21) Appl. No.: 15/145,872

(22) Filed: May 4, 2016

(65) Prior Publication Data

US 2017/0323076 A1  Nov. 9, 2017

(51) Int. Cl.
*G16H 50/30* (2018.01)
*G06Q 50/22* (2018.01)
*G06F 19/00* (2018.01)

(52) U.S. Cl.
CPC ........... *G16H 50/30* (2018.01); *G06F 19/00* (2013.01); *G06Q 50/22* (2013.01); *Y02A 90/22* (2018.01); *Y02A 90/26* (2018.01)

(58) Field of Classification Search
CPC ......... G16H 50/30; G06F 19/00; H04L 43/08; Y02A 90/22; Y02A 90/26; G06Q 50/22
See application file for complete search history.

(56) References Cited

U.S. PATENT DOCUMENTS

| 7,840,421 | B2 | 11/2010 | Gerntholtz |
| 9,141,762 | B2 | 9/2015 | Lev et al. |
| 2009/0265106 | A1* | 10/2009 | Bearman ................. G06Q 10/00 701/300 |
| 2011/0313757 | A1* | 12/2011 | Hoover .................. G06F 17/274 704/9 |
| 2012/0112883 | A1 | 5/2012 | Wallace et al. |
| 2015/0012292 | A1 | 1/2015 | Khan |
| 2015/0100330 | A1 | 4/2015 | Shpits |
| 2017/0286830 | A1* | 10/2017 | El-Yaniv ................... G06F 7/48 |

FOREIGN PATENT DOCUMENTS

| WO | 2008008514 A2 | 1/2008 |
| WO | 2015006858 A1 | 1/2015 |

OTHER PUBLICATIONS

Anderson and May, Infectious Diseases of Humans, Dynamics and Control, 1991, pp. 12-23. (Year: 1991).*

(Continued)

*Primary Examiner* — Christopher L Gilligan
(74) *Attorney, Agent, or Firm* — Ingrid M. Foerster; Edell, Shapiro & Finnan, LLC

(57) ABSTRACT

A method, a processing device, and a computer program product are provided. In various embodiments, one or more processing devices retrieves one or more network communications. The one or more network communications are analyzed, by the at least one processing device, and identifies objects referred to in the network communications having frequent physical contact with different entities. A resulting health risk is produced by aggregating the health risk for each identified object. Based on the resulting health risk, a modified course of action for an entity is advised.

24 Claims, 5 Drawing Sheets

(56) References Cited

OTHER PUBLICATIONS

Friedman et al.,"Social Networks, Risk-Potential Networks, Health, and Disease", http://europepmc.org//, Journal of Urban Health: Bulletin of the New York Academy of Medicine, vol. 78, No. 3, Sep. 2001, pp. 411-418.

Boone et al., "Significance of Fomites in the Spread of Respiratory and Enteric Viral Disease", http://aem.asm.org/content/73/6/1687, Applied and Environmental Microbiology, Jan. 12, 2007, 14 pages.

Network Epidemiology: A Handbook for Survey Design and Data Collection, http://econpapers.repec.org/bookchap/oxpobooks/9780199269013.htm, EconPapers, Dec. 2015, 3 pages.

Bates et al., "Relating Diarrheal Disease to Social Networks and the Geographic Configuration of Communities in Rural Ecuador", http://aje.oxfordjournals.org/content/166/9/1088.short, American Journal of Epidemiology, Aug. 9, 2007, 3 pages.

Carroll et al., "Visualization and analytics tools for infectious disease epidemiology: A systematic review", Journal of Biomedical Informatics 51, Elsevier Inc., 2014, pp. 287-298.

Christakis et al., "Social Network Visualization in Epidemiology", Norsk Epidemiologi 19(1): 5-16, 2009, 23 pages.

Hill et al., "Infectious Disease Modeling of Social Contagion in Networks", http://www.ncbi.nlm.nih.gov/pmc/articles/PMC2973808/, PLoS Computational Biology, Nov. 2010, 39 pages.

\* cited by examiner

ENTER DISEASE OR ILLNESS OF INTEREST } 502

ENTER WHETHER INTERESTED IN INDIVIDUAL, GROUP, COMPANY } 504

FIG.5

ENTER DISEASE OR ILLNESS OF INTEREST

ENTER WHETHER INTERESTED IN INDIVIDUAL, GROUP, COMPANY
  INDIVIDUAL

ENTER USERID OF INDIVIDUAL } 602

FIG.6

ENTER DISEASE OR ILLNESS OF INTEREST

_____

ENTER WHETHER INTERESTED IN INDIVIDUAL, GROUP OR COMPANY
    <u>GROUP</u>

ENTER GROUP ID OR USERIDs SEPARATED BY ";"  } 702

ENTER DISEASE OR ILLNESS OF INTEREST

_____

ENTER WHETHER INTERESTED IN INDIVIDUAL, GROUP OR COMPANY
    <u>COMPANY</u>

ENTER COMPANY NAME } 802

SOCIAL HEALTH RISK ESTIMATION

BACKGROUND

Infectious diseases put a strain on a healthcare system. Viruses, bacteria, parasites and fungi can cause a range of ailments and diseases such as, for example, malaria, measles, respiratory distress, and others, which drive countless visits to healthcare providers. The common cold, alone, is responsible for 75-100 million doctor visits annually. In addition, the diseases and ailments can take a toll on the economy as people call in sick to work.

SUMMARY

According to embodiments of the present invention, a computer-implemented method, a processing device, and a computer program product are provided.

In an aspect of the invention, at least one processing device retrieves one or more network communications. The at least one processing device analyzes the network communications and identifies objects referred to in the network communications having frequent physical contact with different entities. For each identified object, a health risk associated with that object is determined. The health risk for each identified object is aggregated to produce a resulting health risk. A modified course of action is advised for an entity based on the resulting health risk.

BRIEF DESCRIPTION OF THE DRAWINGS

Generally, like reference numerals in the various figures are utilized to designate like components.

FIGS. 5-8 illustrate an example user interface of an embodiment.

DETAILED DESCRIPTION

Figure 1:
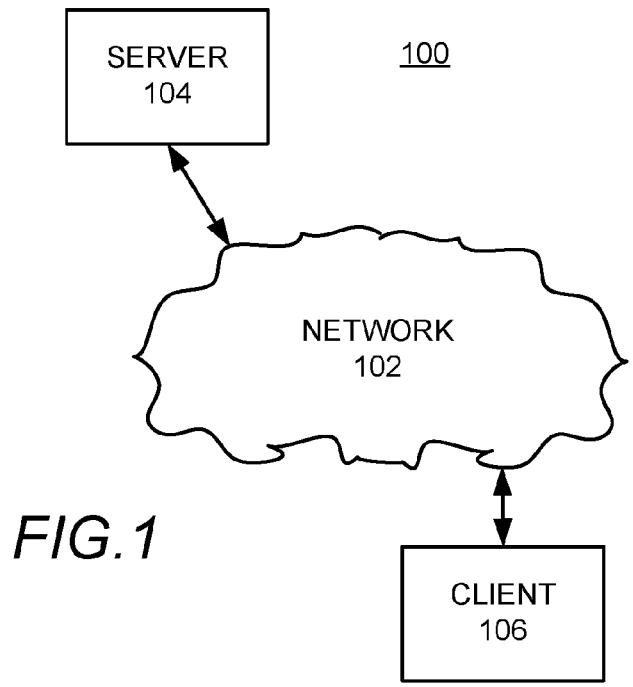
FIG. 1 illustrates an example environment in which various embodiments may be implemented.

With reference now to FIG. 1, an example environment 100 for implementation of embodiments is shown. Example environment 100 may include a server 104, a client 106, and a network 102 connecting client 106 with server 104. Network 102 may include a local area network, a wide area network, a wireless network, the Internet, or a combination thereof.

Figure 2:
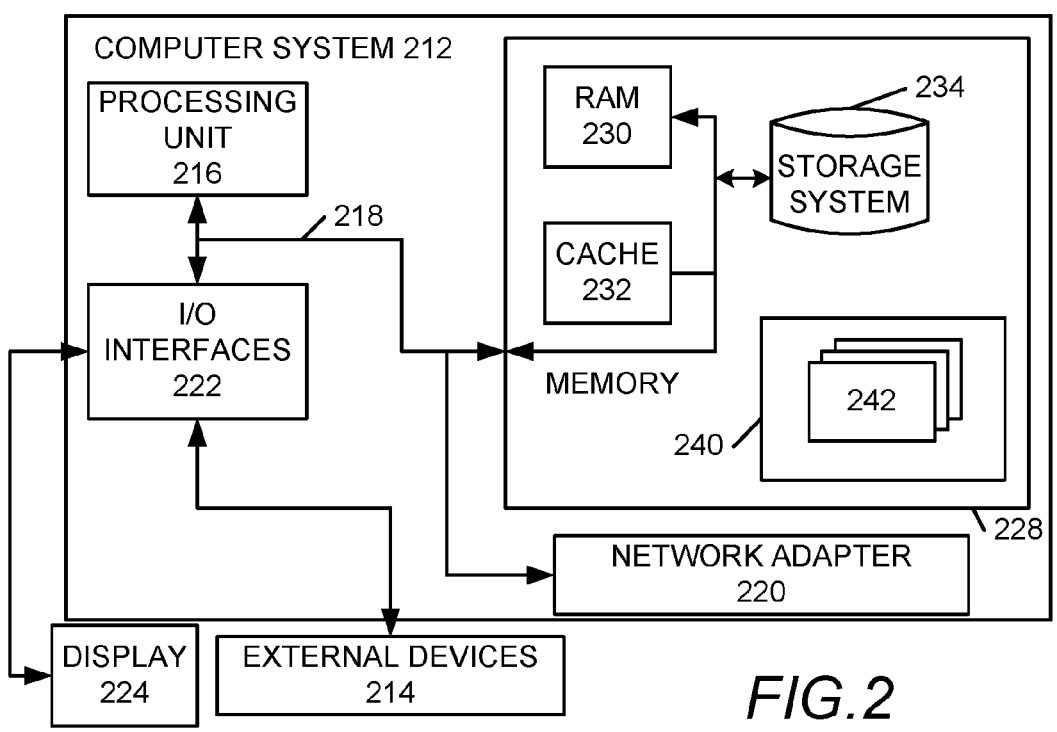
FIG. 2 illustrates an example processing device which may implement embodiments of the invention.

Referring now to FIG. 2, a schematic of an example processing device 210 is shown, which may implement server 104 or client 106. Processing device 210 is only one example of a suitable processing device for server 104 or client 106 of environment 100 of FIG. 1 and is not intended to suggest any limitation as to the scope of use or functionality of embodiments of the invention described herein. Regardless, processing device 210 is capable of being implemented and/or performing any of the functionality set forth herein.

In processing device 210, there is a computer system 212 which is operational with numerous other general purpose or special purpose computing system environments or configurations. Examples of well-known computing systems, environments, and/or configurations that may be suitable for use with computer system 212 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system 212 may be described in the general context of computer system executable instructions, such as program modules, being executed by a computer system. Generally, program modules may include routines, programs, objects, components, logic, data structures, and so on that perform particular tasks or implement particular abstract data types. Computer system 212 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 2, computer system 212 is shown in the form of a general-purpose computing device. Components of computer system 212 may include, but are not limited to, one or more processors or processing units 216, a system memory 228, and a bus 218 that couples various system components including system memory 228 to one or more processors 216.

Bus 218 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system 212 typically includes a variety of computer system readable media. Such media may be any available media that is accessible by computer system 212, and includes both volatile and non-volatile media, and removable and non-removable media.

System memory 228 can include computer system readable media in the form of volatile memory, such as random access memory (RAM) 230 and/or cache memory 232. Computer system 212 may further include other removable/non-removable, volatile/non-volatile computer system storage media. By way of example only, storage system 234 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 218 by one or more data media interfaces. As will be further depicted and described below, memory 228 may include at least one program product having a set (e.g., at least one) of program modules that are configured to carry out the functions of embodiments of the invention.

Program/utility 240, having a set (at least one) of program modules 242, may be stored in memory 228 by way of example, and not limitation, as well as an operating system, one or more application programs, other program modules, and program data. Each of the operating system, the one or more application programs, the other program modules, and program data or some combination thereof, may include an implementation of a networking environment. Program modules 242 generally carry out the functions and/or methodologies of embodiments of the invention as described herein.

Computer system 212 may also communicate with one or more external devices 214 such as a keyboard, a pointing device, a display 224, etc.; one or more devices that enable a user to interact with computer system 212; and/or any devices (e.g., network card, modem, etc.) that enable computer system 212 to communicate with one or more other computing devices. Such communication can occur via Input/Output (I/O) interfaces 222. Still yet, computer system 212 can communicate with one or more networks such as a local area network (LAN), a general wide area network (WAN), and/or a public network (e.g., the Internet) via network adapter 220. As depicted, network adapter 220 communicates with the other components of computer system 212 via bus 218. It should be understood that, although not shown, other hardware and/or software components could be used in conjunction with computer system 212. Examples, include, but are not limited to: microcode, device drivers, redundant processing units, external disk drive arrays, RAID systems, tape drives, and data archival storage systems, etc.

Figure 3:
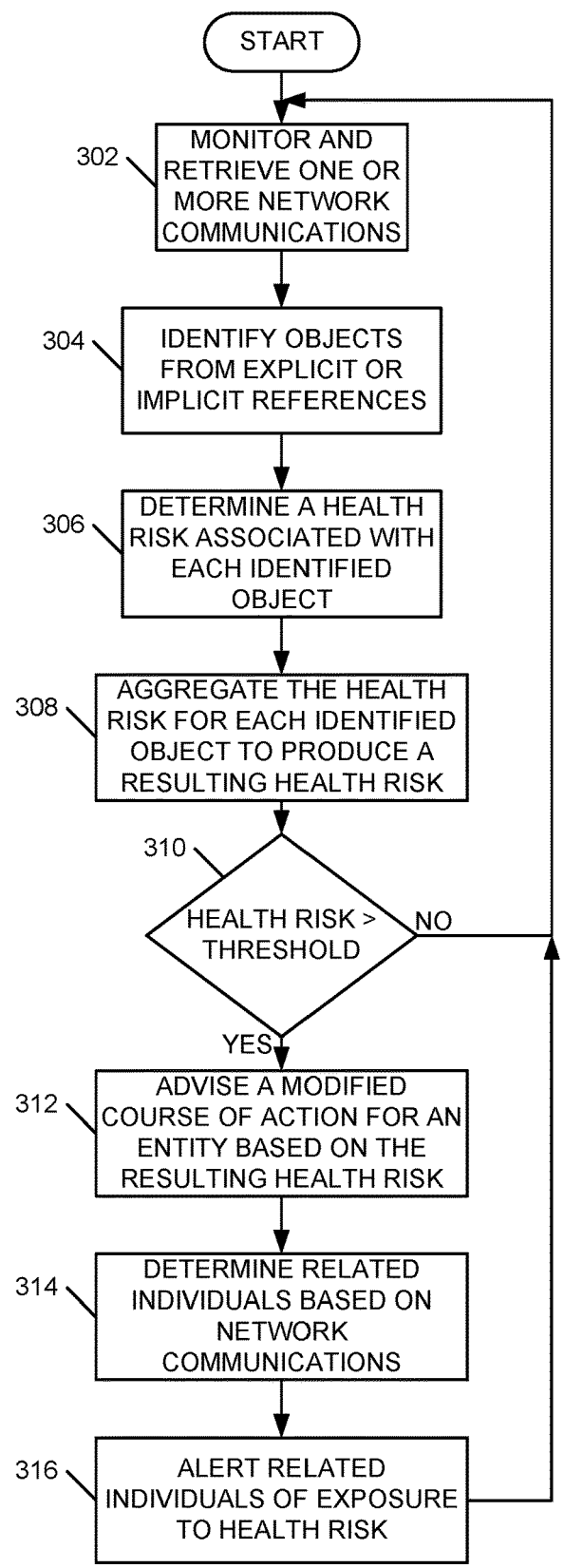
FIG. 3 is a flowchart showing example processing of monitored network communications in one embodiment.

With reference to FIG. 3, example processing in an embodiment is explained. The process may start with server 104 monitoring and retrieving one or more network communications (act 302). The one or more network communications may be communications from a social media network, text messages, emails, or other text-based communications and may include metadata. In various embodiments, a time period during which network communications may be monitored may be based on an incubation period of an ailment or disease of interest. For example, if the ailment of interest is a cold, with an incubation period of 16 hours, network communications may be monitored over a 24 hour period to capture many messages within a reasonable time period. Embodiments may monitor network communications associated with an individual, a group of individuals, a location or a business entity. To explain the example processing, an example is presented in which network communications for an individual, which may include metadata, are being monitored. The communications in this example are shown as {message number, text, location, time} and may include:

{1, "Sitting down to watch the game", Fenway, T1}
{2, "Grab the Cherry Coke to enjoy while Jacob is at bat", Fenway, T2}
{3, "Date Night is phenomenal—Fenway, chicken and cherry coke, but it's on a wobbly table",<empty>, T3}

If the update contains media, the media may be translated to textual representation.

Fomites are frequently touched surfaces, which can be a major contributor to the distribution of infectious diseases. Various embodiments may identify objects from explicit or implicit references (act 304). Embodiments process each communication to determine the fomites. For example, in message 1, "sitting" and a location, "Fenway" imply a seat. In message 2, "Coke" implies a bottle or container. In message 3, "chicken" and "table" are explicit references. Note that message 3 does not include a location. Various embodiments may infer the location based on a nearest neighbor location, or based on included text. For example, if the reference to "Coke" at times T2 and T3 are significantly close (e.g., 2-3 minutes versus 4 hours), embodiments may drop a reference to the message at time T3.

Next, embodiments may determine a health risk associated with each identified object, or fomite (act 306). Initially, each fomite may be assigned a point value. The point value may vary depending upon a location of the fomite. For example, a fomite in a heavily trafficked location may be assigned a higher value than a same fomite at a lightly trafficked location. Going back to our example, sitting at Fenway may be assigned 1 point of risk, a Coke at Fenway may be assigned 2 points of risk, chicken and table at Fenway may be assigned 5 points of risk, and Coke and table at Fenway may be assigned 5 points of risk. The health risk for each identified object, or fomite, may be aggregated to produce a resulting health risk (act 308). In the above example, the individual has an aggregated health risk of 13 points. Assuming, for this example, that the average visitor to Fenway has 10 points of risk, the aggregated health risk for this individual may be considered moderate.

Various embodiments may determine whether the aggregated health risk for an individual is greater than a given threshold or whether any fomites have a health risk greater than the given threshold (act 310). If neither the individual nor the fomites have a health risk greater than the given threshold, then various embodiments may continue to monitor and retrieve network communications (act 302). Otherwise, embodiments may advise a modified course of action for an entity based on the resulting health risk (act 312). For example, if the individual in our example has a health risk greater than the given threshold, then the individual may receive a message from embodiments advising the individual of the health risk and suggesting to the individual to take vitamin C and get plenty of rest. Further, if any of the fomites are determined to have a risk value greater than the given threshold, then an entity responsible for the fomites at the location may receive an alert advising the entity to disinfect these fomites. Embodiments may continue to monitor and retrieve network communications.

In embodiments of the invention, if an individual is determined to have a health risk greater than the threshold, other individuals related to that individual, based on the monitored network communications, may be determined (act 314) and may be alerted (act 316).

One industry standard for context analytics, which may be used in various embodiments, is Unstructured Information Management Architecture (UIMA). UIMA is an architecture that includes software systems for analyzing large volumes of unstructured information in order to discover knowledge that is relevant to an end user. For example, a UIMA application may process text and identify entities, such as persons, places, organizations, or relations such as works-for or located-at.

A UIMA pipeline is a list of individual stages, or annotators, which are run serially. When a document is processed by the UIMA pipeline, a first annotator stage may create annotations covering sections of text. When the first stage is completed, the second annotator stage may then process the text. Each subsequent stage may read annotations created by earlier stages and may add or modify the annotations, thus building up a more complex analysis of contents of the document. The annotations could be for an entire document, a paragraph or sentence, a token or an annotation that one can define by creating a custom dictionary or a parsing rule including, but not limited to, a city, particular keywords, punctuation and font color.

If embodiments are monitoring a location, activities at the location, as determined by monitored network communications, may affect a risk value associated with fomites. For example, as a fomite continues to be touched by individuals, as indicated by the monitored communications, a risk value associated with the fomite may be adjusted upward. On the other hand, as time passes, a risk value associated with each fomite may decrease at a rate consistent with a half-life of an ailment or disease of interest, unless the fomite is continuing to be touched by individuals. As individuals continue to interact with each other and with objects, as indicated by the monitored text, risk values associated with one or more individuals and with touched objects may be adjusted.

Figure 4:
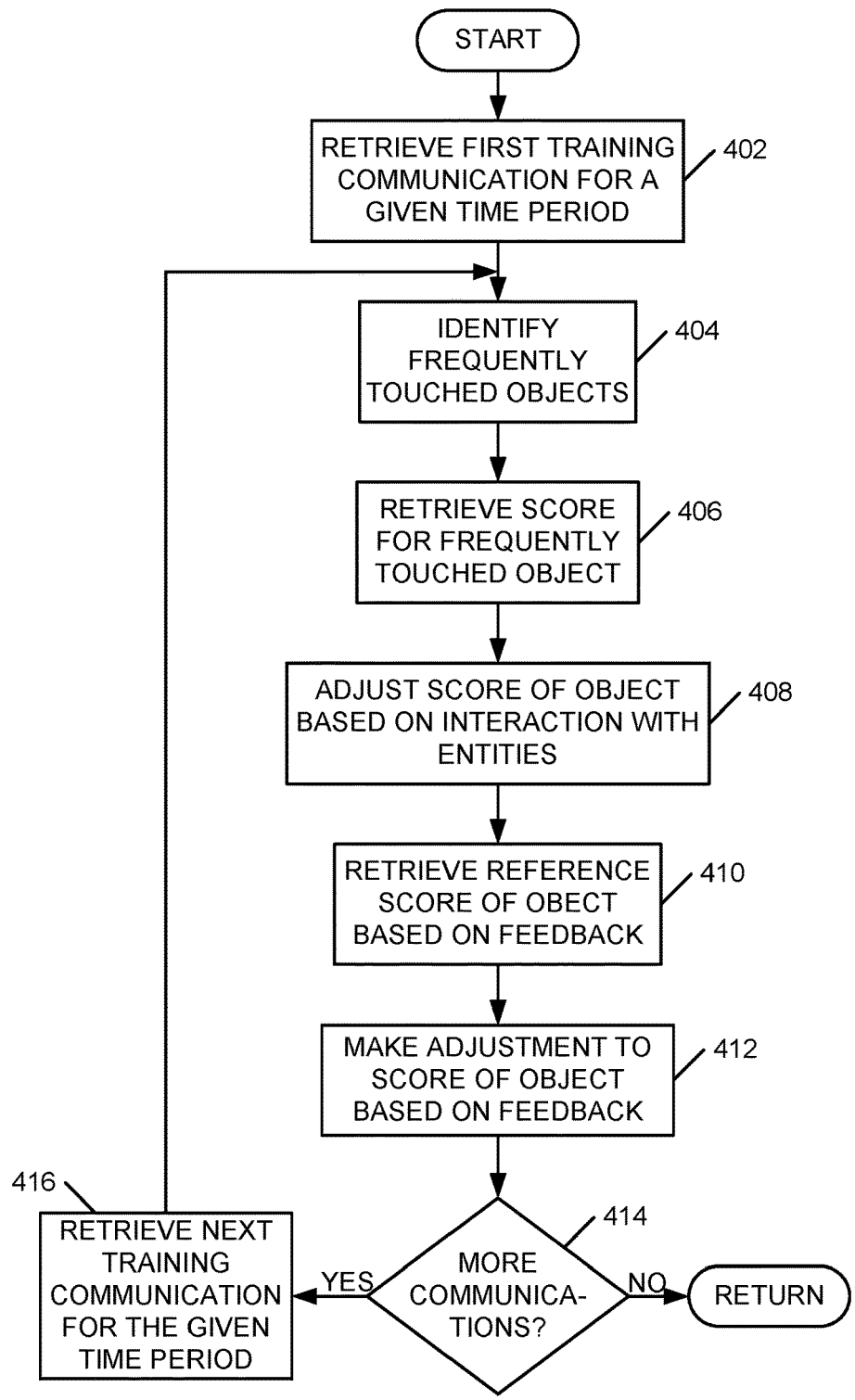
FIG. 4 is a flowchart showing example processing in a training phase of an embodiment.

In some embodiments, risk values for fomites may be learned. FIG. 4 is a flowchart that explains example processing during a training phase of an embodiment. Training is performed using retrieved network communications for which feedback has been received. Experts have reviewed the feedback and assigned reference risk values to fomites for training purposes.

The process may begin with retrieving a first training communication for a given time period (act 402). Initially, all fomites may be assigned a same health risk score. For example, initially, the fomites may be assigned a health risk score of 1 point.

Next, frequently touched objects, or fomites, may be identified by implicit or explicit references in textual network communications (act 404). A health risk score for each identified fomite may then be retrieved (act 406). The health risk score for each identified fomite may then be adjusted based on an entity's interaction with the fomites, where the entity may include an individual, a group of individuals, individuals at a location, or individuals associated with a business entity (act 408). Next, a reference score for each identified fomite, based on feedback, may be retrieved (act 410). The reference scores may have been assigned by experts based on the feedback, including, but not limited to, analysis of network communications of others at a same location during approximately a same time period, as well as any reports regarding outbreaks of illness or disease. For example, if the reference score for a bottle of soda in the work cafeteria is higher than the adjusted health risk score for the bottle of soda, then the health risk score for the bottle of soda in the work cafeteria may be adjusted upward. In one embodiment, the reference score may have an associated incremental score, which may be positive or negative. If the reference score is higher than the health risk score for the bottle of soda in the cafeteria, then the health risk score for that bottle may be incrementally increased for each entity interaction with that bottle during training until the health risk score for that bottle is equal to the reference score. Conversely, if the reference score is lower than the adjusted score for the bottle of soda, then the health risk score of the bottle of soda in the work cafeteria may be adjusted downward by a negative associated incremental score for each entity interaction during training until a lower limit value of the health risk score is reached. (act 412).

If there are no additional communications, the process may be completed. Otherwise, a next training communication for the given time period may be retrieved and acts 404-414 may be repeated.

FIGS. 5-8 are example display screens that show an example user interface for various embodiments. In FIG. 5, a user, or analyst, may be prompted to enter a disease or illness of interest 502. The system may have pre-stored information regarding a number of illnesses or diseases such as, for example, a half-life of the illness or disease, an incubation period, and a contagious factor indicating how contagious the illness or disease is, as well as other information. The analyst may be prompted regarding whether the analyst is interested in monitoring an individual, a group, or a business entity or company 504. If the analyst enters "individual", then the analyst may be prompted to enter a user ID or other identifier of the individual 602 (FIG. 6). If the analyst enters "group", then the analyst may be prompted to enter a group ID or a number of user IDs separated by, for example, a semicolon 702 (FIG. 7). If the user enters "company", the user may be prompted to enter a company name 802 (FIG. 8).

The environment of the present invention embodiments may include any number of computer or other processing systems (e.g., client or end-user systems, server systems, etc.) and databases or other repositories arranged in any desired fashion, where the present invention embodiments may be applied to any desired type of computing environment (e.g., cloud computing, client-server, network computing, mainframe, stand-alone systems, etc.). The computer or other processing systems employed by the present invention embodiments may be implemented by any number of any personal or other type of computer or processing system (e.g., desktop, laptop, PDA, mobile devices, etc.), and may include any commercially available operating system and any combination of commercially available and custom software (e.g., browser software, communications software, server software, etc.). These systems may include any types of monitors and input devices (e.g., keyboard, mouse, voice recognition, etc.) to enter and/or view information.

It is to be understood that the software of the present invention embodiments may be implemented in any desired computer language and could be developed by one of ordinary skill in the computer arts based on the functional descriptions contained in the specification and flowcharts illustrated in the drawings. Further, any references herein of software performing various functions generally refer to computer systems or processors performing those functions under software control. The computer systems of the present invention embodiments may alternatively be implemented by any type of hardware and/or other processing circuitry.

The various functions of the computer or other processing systems may be distributed in any manner among any number of software and/or hardware modules or units, processing or computer systems and/or circuitry, where the computer or processing systems may be disposed locally or remotely of each other and may communicate via any suitable communications medium (e.g., LAN, WAN, Intranet, Internet, hardwired, modem connection, wireless, etc.). For example, the functions of the present invention embodiments may be distributed in any manner among the various systems, and/or any other intermediary processing devices. The software and/or algorithms described above and illustrated in the flowcharts may be modified in any manner that accomplishes the functions described herein. In addition, the functions in the flowcharts or description may be performed in any order that accomplishes a desired operation.

The software of the present invention embodiments may be available on a non-transitory computer useable medium (e.g., magnetic or optical mediums, magneto-optic mediums, floppy diskettes, CD-ROM, DVD, memory devices, etc.) of a stationary or portable program product apparatus or device for use with stand-alone systems or systems connected by a network or other communications medium.

The communication network may be implemented by any number of any type of communications network (e.g., LAN, WAN, Internet, Intranet, VPN, etc.). The computer or other processing systems of the present invention embodiments may include any conventional or other communications devices to communicate over the network via any conventional or other protocols. The computer or other processing systems may utilize any type of connection (e.g., wired, wireless, etc.) for access to the network. Local communication media may be implemented by any suitable communication media (e.g., local area network (LAN), hardwire, wireless link, Intranet, etc.).

The system may employ any number of any conventional or other databases, data stores or storage structures (e.g., files, databases, data structures, data or other repositories, etc.) to store information. The database system may be implemented by any number of any conventional or other databases, data stores or storage structures (e.g., files, databases, data structures, data or other repositories, etc.) to store information. The database system may be included within or coupled to a server and/or client systems. The database systems and/or storage structures may be remote from or local to the computer or other processing systems, and may store any desired data.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises", "comprising", "includes", "including", "has", "have", "having", "with" and the like, when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or act or carry out combinations of special purpose hardware and computer instructions.

The invention claimed is:

1. A method of learning health risk values of objects during a training phase and monitoring text-based network communications for a health risk, the method comprising:
training at least one processing device to learn a health risk value for each identified object in a plurality of text-based training communications, the training further comprising:
performing, by the at least one processing device, for each respective text-based training communication:
retrieving a respective text-based training communication for a given time period and a given location,
analyzing the respective text-based training communication to identify a respective object explicitly or implicitly referenced in the text-based training communication,
retrieving a corresponding health risk value for the identified respective object,
adjusting the health risk value for the identified respective object based on an interaction by one or more entities with the identified respective object;
retrieving a reference health risk value for the identified respective object, the reference health risk value being based on feedback, and
incrementally adjusting the health risk value for the identified respective object based on the reference health risk value for the identified respective object;
performing, by the at least one processing device, after completion of the training:
retrieving one or more text-based network communications associated with an entity of interest, the entity of interest being one from an individual, a group of individuals, individuals associated with a business entity, and individuals at a location,
analyzing the one or more text-based network communications and identifying one or more objects referred to in the one or more text-based network communications having frequent physical contact with one or more different entities,
determining a health risk value associated with each of the one or more identified objects based on the training,
aggregating the health risk value for the each of the identified one or more objects to produce a resulting health risk value for the entity of interest, the resulting health risk value being related to the health risk, and
performing at least one action when the resulting heath risk value is greater than a threshold, wherein:
the plurality of text-based training communications being originally sent from respective second processing devices via a network, and
the one or more text-based network communications being originally sent from respective third processing devices via a network.

2. The method of claim 1, wherein the one or more text-based network communications include one or more from a group of social network data, electronic mail, and instant messaging messages.

3. The method of claim 1, wherein the at least one action further comprises:
advising a modified course of action for the entity of interest based on the resulting health risk value.

4. The method of claim 3, wherein the advising a modified course of action for the entity of interest based on the resulting health risk value further comprises at least one of:
advising an entity responsible for at least one identified object to remediate the health risk of the at least one identified object; and advising the entity of interest to take action to lessen an effect of infection to the entity of interest.

5. The method of claim 1, wherein the at least one action further comprises:
determining related individuals based on the one or more text-based network communications and alerting the related individuals of exposure to the health risk.

6. The method of claim 1, further comprising:
adjusting the resulting health risk value based on an amount of entity interaction.

7. The method of claim 1, further comprising:
modeling a half-life of an illness, wherein the resulting health risk value is represented as a half-life.

8. The method of claim 1, wherein the reference health value for respective identified objects is based on one or more text-based network communications of others for the given time period at the given location.

9. At least one processing device for learning health risk values of objects during a training phase and monitoring text-based network communications for a health risk, each of the at least one processing device comprising:
at least one processor; and
at least one memory connected with the at least one processor, wherein the at least one memory has instructions for the at least one processor to perform a method comprising:
training the at least one processing device to learn a health risk value for each identified object in a plurality of text-based training communications, the training further comprising:
performing, by the at least one processing device, for each respective text-based training communication:
retrieving a respective text-based training communication for a given time period and a given location,
analyzing the respective text-based training communication to identify a respective object explicitly or implicitly referenced in the text-based training communication,
retrieving a corresponding health risk value for the identified respective object,
adjusting the health risk value for the identified respective object based on an interaction by one or more entities with the identified respective object,
retrieving a reference health risk value for the identified respective object, the reference health risk value being based on feedback, and
incrementally adjusting the health risk value for the identified respective object based on the reference health risk value for the identified respective object,
performing, by the at least one processing device, after completion of the training:
retrieving one or more text-based network communications associated with an entity of interest, the entity of interest being one from an individual, a group of individuals, individuals associated with a business entity, and individuals at a location,
analyzing the one or more text-based network communications and identifying one or more objects referred to in the one or more text-based network communications having frequent physical contact with one or more different entities,
determining a health risk value associated with each of the one or more identified objects based on the training,
aggregating the health risk value for the each of the identified one or more objects to produce a resulting health risk value for the entity of interest, the resulting health risk value being related to the health risk, and
performing at least one action when the resulting heath risk value is greater than a threshold,
wherein:
the plurality of text-based training communications being originally sent from respective second processing devices via a network, and
the one or more text-based network communications being originally sent from respective third processing devices via a network.

10. The at least one processing device of claim 9, wherein the network communications include one or more from a group of social network data, electronic mail, and instant messaging messages.

11. The at least one processing device of claim 9, wherein the at least one action further comprises:
advising a modified course of action for the entity of interest based on the resulting health risk value.

12. The at least one processing device of claim 11, wherein the advising a modified course of action for the entity of interest based on the resulting health risk value further comprises at least one of:
advising an entity responsible for at least one identified object to remediate the health risk of the at least one identified object; and
advising the entity of interest to take action to lessen an effect of infection to the entity of interest.

13. The at least one processing device of claim 9, wherein the at least one action further comprises:
determining related individuals based on the one or more text-based network communications and alerting the related individuals of exposure to the health risk.

14. The at least one processing device of claim 9, wherein the method further comprises:
adjusting the resulting health risk value based on an amount of entity interaction.

15. The at least one processing device of claim 9, wherein the method further comprises:
modeling a half-life of an illness, wherein the resulting health risk value is represented as a half-life.

16. The at least one processing device of claim 9, wherein the reference health value for respective identified objects is based on one or more text-based network communications of others for the given time period at the given location.

17. A computer program product for learning health risk values of objects during a training phase and monitoring text-based network communications for a health risk comprising:
at least one non-transitory computer readable storage medium having computer readable program code embodied therewith for execution on a processing system, the computer readable program code being configured to be executed by the processing system to:
train the processing system to learn a health risk value for each identified object in a plurality of text-based training communications, the training further comprising:
perform, by the processing system, for each respective text-based training communication:

retrieving a respective text-based training communication for a given time period and a given location, analyzing the respective text-based training communication to identify a respective object explicitly or implicitly referenced in the text-based training communication, retrieving a corresponding health risk value for the identified respective object, adjusting the health risk value for the identified respective object based on an interaction by one or more entities with the identified respective object, retrieving a reference health risk value for the identified respective object, the reference health risk value being based on feedback, and incrementally adjusting the health risk value for the identified respective object based on the reference health risk value for the identified respective object;

perform, by the processing system, after completion of the training:

retrieving one or more text-based network communications associated with an entity of interest, the entity of interest being one from an individual, a group of individuals, individuals associated with a business entity, and individuals at a location;

analyzing the one or more text-based network communications and identifying one or more objects referred to in the one or more text-based network communications having frequent physical contact with one or more different entities, determining a health risk value associated with each of the one or more identified objects based on the training, aggregating the health risk value for the each of the identified one or more objects to produce a resulting health risk value for the entity of interest, and performing at least one action when the resulting heath risk value is greater than a threshold, wherein:

the plurality of text-based training communications being originally sent from respective second processing devices via a network, and the one or more text-based network communications being originally sent from respective third processing devices via a network.

18. The computer program product of claim 17, wherein the one or more network communications include one or more from a group of social network data, electronic mail, and instant messaging messages.

19. The computer program product of claim 17, wherein the at least one action further comprises:

advising a modified course of action for the entity of interest based on the resulting health risk value.

20. The computer program product of claim 19, wherein the advising a modified course of action for the entity of interest based on the resulting health risk value further comprises at least one of:

advising an entity responsible for at least one identified object to remediate the health risk of the at least one identified object; and advising the entity of interest to take action to lessen an effect of infection to the entity of interest.

21. The computer program product of claim 17, wherein the computer readable program code is further configured to be executed by the processing system to:

determine related individuals based on the one or more text-based network communications and alert the related individuals of exposure to the health risk.

22. The computer program product of claim 17, wherein the computer readable program code is further configured to be executed by the processing system to:

adjust the resulting health risk value based on an amount of entity interaction.

23. The computer program product of claim 17, wherein the reference health value for respective identified objects is based on one or more text-based network communications of others for the given time period at the given location.

24. A system for learning health risk values of objects during a training phase and monitoring network communications for a health risk, the system comprising:

at least one server connected to a network, wherein the at least one server is configured to:

train the at least one server to learn a health risk score for each identified object in a plurality of text-based training communications, the training further comprising:

performing, by the at least one server, for each respective text-based training communication:

retrieving a respective text-based training communication for a given time period and a given location, analyzing the respective text-based training communication to identify a respective object explicitly or implicitly referenced in the text-based training communication, retrieving a corresponding health risk value for the identified respective object, adjusting the health risk value for the identified respective object based on an interaction by one or more entities with the identified respective object, retrieving a reference health risk value for the identified respective object, the reference health risk value being based on feedback, and incrementally adjusting the health risk value for the identified respective object based on the reference health risk value for the identified respective object;

perform, by the at least one server, after completion of the training:

retrieving one or more text-based network communications associated with an entity of interest, the entity of interest being one from an individual, a group of individuals, individuals associated with a business entity, and individuals at a location, analyzing the one or more text-based network communications and identifying one or more objects referred to in the one or more text-based network communications having frequent physical contact with one or more different entities;

determining a health risk value associated with that object each of the one or more identified objects based on the training, aggregating the health risk value for the each of the identified one or more objects to produce a resulting health risk value for the entity of interest, and performing at least one action when the resulting heath risk value is greater than a threshold, the resulting health risk value being related to the health risk, wherein:

the plurality of text-based training communications being originally sent from respective second processing devices via a network, and the one or more text-based network communications being originally sent from respective third processing devices via a network.

\* \* \* \* \*